United States Patent [19]

Gugel

[11] 4,117,733

[45] Oct. 3, 1978

[54] TEST SYSTEM CARRIER FOR ULTRASONIC TESTING OF NOZZLE SEAMS, PIPE CONNECTION SEAMS AND NOZZLE CORNERS IN PRESSURE VESSELS, PARTICULARLY REACTOR PRESSURE VESSELS OF NUCLEAR POWER PLANTS

[75] Inventor: Georg Gugel, Kalchreuth, Germany

[73] Assignee: Kraftwerk Union Aktiengesellschaft, Mulheim, Germany

[21] Appl. No.: 752,299

[22] Filed: Dec. 20, 1976

[30] Foreign Application Priority Data

Dec. 22, 1975 [DE] Fed. Rep. of Germany ....... 2557992

[51] Int. Cl.$^2$ ............................................. G01N 29/04
[52] U.S. Cl. ........................................ 73/634; 73/640; 176/19 R
[58] Field of Search .................... 73/67.8 S; 176/19 R

[56] References Cited

U.S. PATENT DOCUMENTS

| 3,809,607 | 5/1974 | Murray et al. | 73/67.8 S X |
| 3,862,578 | 1/1975 | Schluter | 73/67.8 S X |
| 3,943,756 | 3/1976 | Aubert et al. | 73/67.8 S X |

*Primary Examiner*—James J. Gill
*Attorney, Agent, or Firm*—Herbert L. Lerner

[57] ABSTRACT

Test system carrier for ultrasonic testing of pressure vessels, the carrier being supported at the end of a telescopic tube for executing stroke and rotary motions in or about the axis of a nozzle, the telescopic tube being adjustably mounted on the central mast of a central-mast manipulator so as to be adjustable in elevation and rotatable about the axis of the central mast as well as about its own axis includes, in combination, an inner-periphery test-head carrier displaceable along the axis of a nozzle and radially thereto for ultrasonically testing seams formed in the nozzle and seams between pipe connections and the nozzle as well as zones adjacent thereto; a tiltable lever, test head means carried by the lever, the lever being movable so as to bring the test head means into contact with surfaces at the end of the nozzle, the corner of the nozzle and the inner periphery of the nozzle and movable in test tracks within the entire respective peripheral angle nozzle thereof; the pivot axis of the lever being shiftable axially away from the telescoping tube, and the angular position of the lever with respect to the telescoping tube being variable for contacting the respective test tracks, the lever being controllably movable into an inward folded-up seat position so that the test system carrier with the inner-periphery test-head carrier is axially displaceable unobstructedly through the nozzle.

10 Claims, 9 Drawing Figures

TEST SYSTEM CARRIER FOR ULTRASONIC TESTING OF NOZZLE SEAMS, PIPE CONNECTION SEAMS AND NOZZLE CORNERS IN PRESSURE VESSELS, PARTICULARLY REACTOR PRESSURE VESSELS OF NUCLEAR POWER PLANTS

Test system carrier for ultrasonic testing of pressure vessels are known in a great variety of constructions. In particular, such carriers for ultrasonic testing of reactor pressure vessels of nuclear power plants are known. The requirements for starting-up and operating nuclear power plants call for periodic checks of the integrity of the components of the reactor circulating cooling loop and, in particular, of the reactor pressure vessel and the nozzles or pipe unions thereof. In this connection, the ultrasonic testing mentioned is particularly well suited because it is a non-destructive testing method. A test system carrier for the ultrasonic testing of nozzle or union seams and pipe connection seams in reactor pressure vessels is known (German Published Prosecuted Application DT-AS No. 2 325 388) wherein the carrier is supported at the end of a telescopic tube for executing stroke or lift and rotating motions in or about the nozzle or union axis, the telescopic tube being supported at the central mast of a central-mast manipulator, and being adjustable in elevation as well as rotatable about the axis of the central mast and about its own axis. Such a test system carrier is also shown in German Published Non-Prosecuted Application DT-OS No. 2 154 015, wherein the test system carrier associated with a telescopic tube can only test either the nozzle or union seams or the pipe connection seams from the inner periphery of the nozzle or union to determine so-called transverse faults. However, the regions of the nozzle or union corners cannot be simultaneously tested with this test system carrier, nor is it possible to use this test system carrier for so-called longitudinal fault testing. The latter testing must instead be carried out with special heads from the nozzle or union inlet region, which requires another test system carrier with a separate testing head system on another telescoping arm. This means that a new approach to the start-up, centering, adjustment and measuring operations is necessary. The same disadvantages also apply to the test system carrier according to the German petty patent DT-GE Nos. 7 326 627 (testing of the corner region of the nozzle or union) and 7 326 591 (testing of the inner periphery of the nozzle or union).

It is therefore an object of the invention to provide a test system carrier for ultrasonic testing in pressure vessels, particularly reactor pressure vessels of nuclear power plants which avoids the foregoing disadvantages of the heretofore known devices of this general type and with which it is possible to perform tests of nozzle or union seams, pipe connection seams and nozzle or union corners with a single telescopic arm and, accordingly, with one centering operation of that arm. It is also an object of the invention, in particular, to provide such a test system carrier which is manipulatable precisely and easily from the central mast i.e. movable in a reproducible manner into the starting position, to center it and to direct it into the individual test positions for scanning the test tracks in the nozzle or union corner areas and nozzle or union areas.

With the foregoing and other objects in view, there is provided in accordance with the invention, a test system carrier for ultrasonic testing of nozzle seams, pipe connection seams and nozzle corners in pressure vessels, the carrier being supported at the end of a telescopic tube for executing stroke and rotary motions in or about the axis of the nozzle, the telescopic tube being adjustably mounted on the central mast of a central-mast manipulator so as to be adjustable in elevation and rotatable about the axis of the central mast as well as about its own axis includes, in combination, at least one inner-periphery test-head carrier displaceable along the axis of a nozzle and radially thereto for ultrasonically testing seams formed in the nozzle and seams between pipe connections and the nozzle as well as zones adjacent thereto; a tiltable test-head carrier having at least one drag lever forming a pivotal attachment of the test system carrier, the drag lever having an inner and an outer lever arm, tilting drive means coupled to the inner lever arm for tilting the same, test head means carried by the outer lever for testing the nozzle corners, the drag lever being successively movable so as to bring the test head means into contact with surfaces at the end of the nozzle, the corner of the nozzle and the inner periphery of the nozzle and movable in test tracks within the entire respective peripheral angle range thereof; the test head means, in an outward unfolded operating position of the drag lever encompassing an operating angle $\alpha$, being engageable with the respective test tracks to be contacted, the pivot axis of the drag lever being shiftable axially away from the telescoping tube and the angular position of the drag lever with respect to the telescoping tube being variable for contacting the respective test tracks, the drag lever being controllably movable into an inward folded-up rest position wherein the arms thereof are disposed on a diameter that is smaller than the diameter of the inner periphery of the nozzle so that the test system carrier with the inner-periphery test-head carrier is axially displaceable unobstructedly through the nozzle. The advantages derivable from the application of the invention are seen particularly in the fact that considerable time-saving can be realized with the test system in the ultrasonic testing of the nozzle regions of reactor pressure vessels, since after the test system carrier is once properly oriented, all test tracks can be run successively in a reproducible manner without requiring the use of a second test system carrier. The shortening of the so-called setup time means a shortening of the overall test periods and therefore, of the shutdown time of the nuclear reactor installation. With the test system carrier according to the invention, it is also possible, in an advantageous manner, to perform a nozzle-seam longitudinal-fault test. This longitudinal-fault test is particularly important for the nozzle connection seam, since so-called circular-disk reflectors which are oriented normal to the axis are difficult to detect with conventional ultrasound test heads which respond to transverse faults. Therefore, in addition to a first inner-periphery test-head carrier, a second such carrier for determining longitudinal faults can be provided; it is particularly advantageous, however, to assign the longitudinal-fault testing to the test head system of a drag lever, since the most favorable direction of incidence of the ultrasonic waves can be realized in a relatively simple manner from the end of the nozzle. This means that the drag lever is equipped with a test head system for longitudinal-fault testing besides its test head system for nozzle corner testing.

In accordance with another feature of the invention, there is provided another drag lever having test head means for testing longitudinal faults, the last-mentioned test head means being movable into contact with the ends of the nozzle and movable over test tracks in peripheral direction of the nozzle, test tracks being disposed over entire annular zones of the end of the nozzle lying in a projection of the nozzle seam.

Such a second drag lever has the advantage that the testing capacity of the drag lever system can be increased. In particular, the two drag levers can be mounted and disposed in such a manner that the two test head sytems thereof lie approximately on one diameter, so that simultaneous operation of both test head systems without mutual interference may be possible under certain conditions. It is a further advantage in this connection that the two drag lever systems can be arranged practically statically balanced, which has a favorable effect upon the accuracy of the testing.

According to a further feature of the invention, the test system, includes an ultrasonic centering eye disposable within the bore of the nozzle at a forward end of the test system carrier for centering the latter within the nozzle bore, the eye being mounted on a free end of a radial arm forming part of the test system carrier and being pivotable in peripheral direction, linkage means for inserting the eye into the nozzle bore forward of other test systems of the test system carrier so that the other test systems are displaceable into the test position thereof only if the axis of the test system carrier and the axis of the telescoping tube are centered within the nozzle bore.

The ultrasonic eye can be moved in the direction of the nozzle axis by means of a parallel linkage, especially, which engages a clamping member carrying the radial arm. This linkage may furthermore be mounted axially parallel to the telescopic tube in such a manner that the linkage can not only be moved in and out axially, but the radial arm can be unfolded outwardly and folded-up inwardly as well by means of relative displacement of the two parts of the linkage. The operation of the linkages is advantageously effected by pneumatic means. Such an ultrasonic eye transmits ultrasonic pulses and also has a receiver for the ultrasonic signals reflected from the inner wall surface of the nozzle, so that corrective values for the centered positioning of the telescoping arm can be derived from deviations in the transmission time of the received ultrasonic signals at different angular positions of the radial arm. Since the centering as well as the subsequent ultrasonic testing is performed under water, the ultrasonic eye, therefore, measures the range or course thereof in water.

According to an additional feature of the invention, the pivot axis of the drag lever is disposed respectively eccentric to the axis of the telescoping tube and is formed of a radial projection secured to the outer periphery of a housing for the test system carrier, and a compressed-air cylinder fastened to the housing for the test system carrier, the cylinder having a drive member linked to the inner lever arm of the drag lever, respectively. Such a construction would also permit the attachment of more than two drag levers without any mutual interference therefrom due to the tilting motions thereof.

In accordance with an additional feature of the invention the inner lever arm of the drag lever is disposed at an angle to a longitudinal axis of the drag lever defined by the outer lever arm so that the pivot angle range of the drag lever, which encompasses the operating range and the rest position of the drag lever, is convertible by the tilting drive means in the range of the maximal torque thereof.

In accordance with an added feature of the invention, the test head means carried by the first-mentioned drag lever comprises at least two universally mounted test heads disposed at different diameters for testing a nozzle contour having two test track zones offset axially and radially from one another, the universally mounted test heads being adapted to test nozzle seams for longitudinal faults.

In addition to the versatility thereof, such a construction has the advantage also that it can easily be balanced statically. Fine adjustment in peripheral direction is thereby made possible without additional torsion moments and without the tendency to hunt or oscillate.

In accordance with yet another feature of the invention, the test system carrier includes a pair of inner periphery test-head carriers having respective rows of test heads located diametrically opposite one another in the testing position thereof within a nozzle bore, the pair of inner-periphery test-head carriers having respective base members forming a secured part of the test system carrier and being disposed eccentric to the longitudinal axis thereof, the base members extending parallel to and overlapping one another in the diametral direction, the test heads of the rows being associated with different functional groups serving to test the nozzle seam and the seam between the pipe connection and the nozzle.

In accordance with yet a further feature of the invention, the test head means comprise a plurality of test heads, and respective cardanic tilting lever mechanisms are included whereon the test heads are mounted.

In accordance with an additional feature of the invention, the test heads include inner-periphery test heads, a respective base member having a head member seated at an outer end thereof, the cardanic tilting lever mechanisms for the respective inner-periphery test heads being fastened to the respective base member, the base member, head member and tilting lever mechanism for the inner periphery test heads, as viewed in axial direction of the nozzle being disposed substantially point-symmetrically to one another and statically balanced.

In accordance with a concomitant feature of the invention, the test system carrier includes a plurality of the drag levers, and the test head means comprise respective test heads for the drag levers, and further including a slide for the respective test heads mounted on a cardanic link of an angle lever, the angle lever having a base point and the slide having a contact surface disposed at a constant spacing with respect to the neutral position thereof from the base point, there being no spring travel path between the slide and the base point in the spacing direction, the respective test head being cardanically mounted at the slide, the test head and the respective cardanic mounting thereof being seated on a tilting lever spring-loaded in direction of applied force.

Other features which are considered as characteristic for the invention are set forth in the appended claims.

Although the invention is illustrated and described herein as embodied in test system carrier for ultrasonic testing of nozzle seams, pipe connection seams and nozzle corners in pressure vessels, particularly reactor pressure vessels of nuclear power plants, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings, in which:

FIG. 1 is a diagrammatic, partially cross-sectional view of the test system carrier according to the invention, with its drag levers in operating position and with its inner-periphery test head carrier part in an intermediate position, before it is placed on the test zones proper; half of the cross section of an outlet nozzle being shown in the upper part of the figure, and half of the cross section of an inlet nozzle in the lower part of the figure, so that the test conditions with respect to these two types of nozzles can be explained with reference to a single figure;

Figure 1:
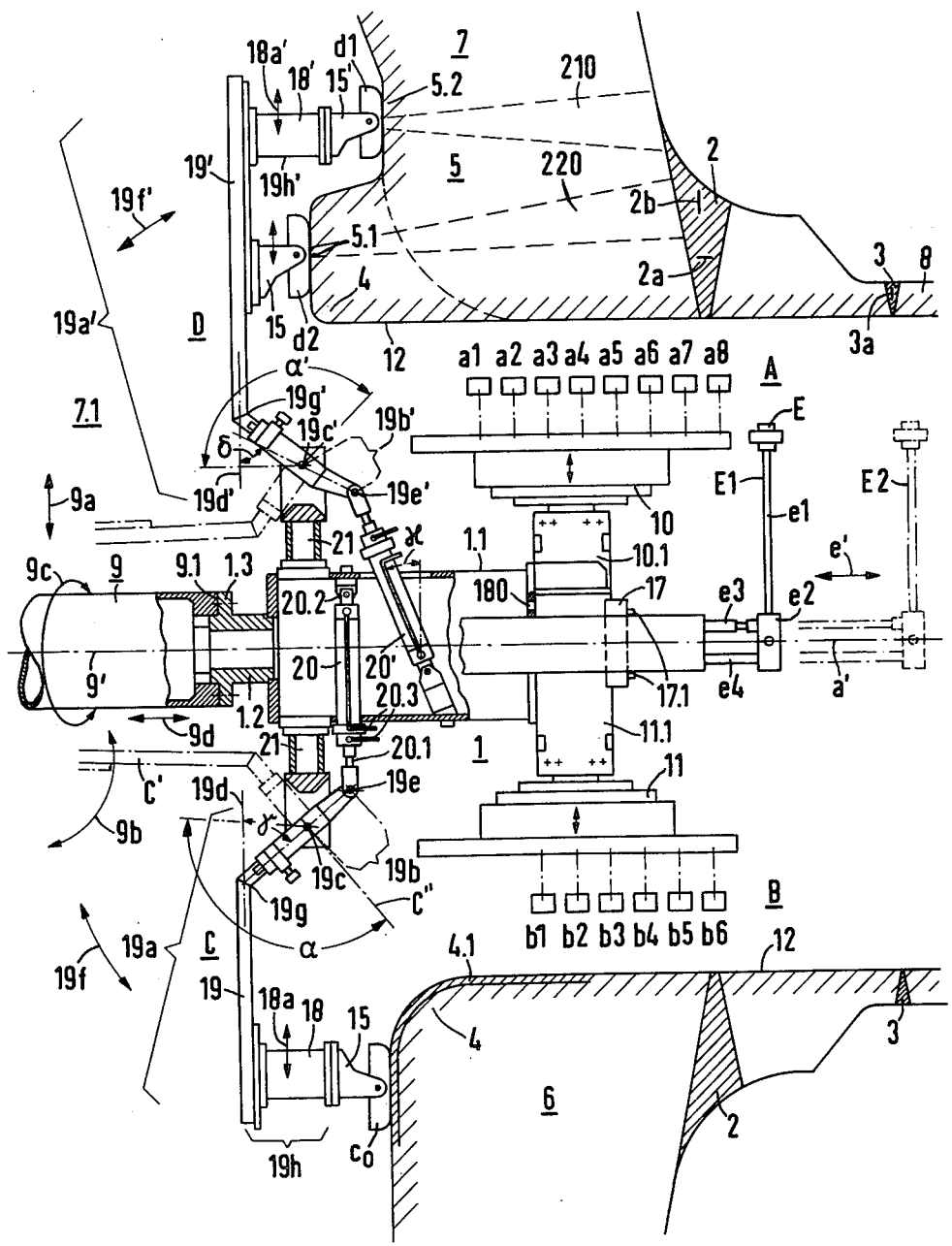

Referring now to the figures of the drawing and first, particularly, to FIG. 1 thereof, there is shown the test system carrier 1 of the invention in its entirety, which serves for testing nozzle or union seams or joints 2, pipe connection seams or joints 3 and nozzle or union corner regions 4 of an outlet nozzle or union 5 (upper part of FIG. 1) and an inlet nozzle or union 6 (lower part of FIG. 1). The nozzles 5, 6, which belong to a reactor pressure vessel 7, that is not shown in detail, are connected in a conventional manner to reactor coolant lines indicated at 8. The interior of the reactor pressure vessel is designated 7.1. Primary coolant, which is delivered by a non-illustrated reactor coolant pump, flows through the inlet nozzles 6 into the reactor pressure vessel, where it is conducted through cooling channels of the non-illustrated reactor core and is pumped subsequently through the outlet nozzles 5 and through heat exchanger tubes to the suction side of the pump, which pumps the coolant (which the case of pressurized-water reactors is light water) back into the reactor pressure vessel in a closed loop, after the coolant has been cooled in the heat exchanger. The existing safety requirements for this primary cooling loop are very stringent and it is therefore important that the seams 2, 3 and the austenitic cladding in the region of the nozzle corners 4 are checked for faults i.e. particularly incipient cracks. In the nozzle seams 2, transverse faults 2a or longitudinal faults 2b can occur, in principle, or corresponding mixed faults can occur. The transverse faults 2a in the case of the nozzle seams 2 and the faults 3a which might occur in the pipe connection seams 3, the detection of which is simpler because of the smaller radiation penetration depth, are detected by the test systems generally designated A and B. If present, these faults are localized as to size and position. The cladding of the nozzle corner 4 indicated at 4.1 is examined for possible incipient cracks by the testing system C. Possible longitudinal faults 2b can be tracked down by means of the test system D. This ultrasonic test is performed under water, with the reactor pressure vessel empty. For this purpose, a telescopic tube 9 is mounted on a non-illustrated central mast of a conventional central-mast manipulator and is supported, adjustably in height by the latter (arrow 9a), and rotatably about the central mast axis (arrow 9b) as well as rotatably about its own axis 9' (arrow 9c). In addition, the telescopic tube 9 can carry out a stroke in the directions of insertion and removal of the nozzles 5, 6 corresponding to arrow 9d. In the position illustrated in FIG. 1, the axis 9' of the telescopic tube 9 is identical with the nozzle axis a', since the test system carrier 1 is shown in the centered position thereof. All the movements of the telescopic tube 9 of the test system carrier 1 can be executed from a central control console i.e. by remote control. The telescopic tube 9 is precisely supported relative to the other telescopic tubes and the central mast manipulator, so that practically no deviation from the horizontal is encountered, and pneumatic control is possible. The test system carrier 1 has a tubular base member 1.1 with an axial extension 1.2, the flange 1.3 of which is fitted to the end face 9.1 of the end of the telescopic tube 9. The base member 1.1 of the test system carrier 1 supports the hereinaftermentioned test systems A, B, C, D and, furthermore, the ultrasonic eye E. The test system A comprises an inner-periphery test head carrier 10, which is mounted to the base body 1.1 and is equipped with test heads $a1$ to $a8$, diagrammatically indicated by outlines and center lines. The construction and function of these test heads will be explained in detail hereinbelow. A second inner-periphery test head carrier 11 for the test system B is likewise fastened to the base member 1.1 and carries a number of test heads $b1$ and $b6$. As shown particularly in FIG. 2, two inner-periphery test head carriers 10, 11 are provided, the test head rows $a1$ to $a8$ and $b1$ to $b6$ being located opposite each other on a diameter 12.1 in the test position i.e. when making contact at the inner periphery 12 of the nozzle. The test head carriers 10, 11 are fastened with their base members 10.1, 11.1 overlapping (extending into overlap zone 13) in direction parallel to the diameter 12.1 (longitudinal axes 10.2, 11.2) and eccentrically to the longitudinal axis $a'$ of the test system carrier 1. The eccentricity is identified at 14. The test heads, generally designated $a$ and $b$, are each supported in separate gimbal or cardanic tilting lever or rocker arm mechanisms 15 which supply the required spring travel and the necessary spring contact force. The mechanisms 15 are mounted at the outer ends of head pieces 16, with the mechanism 15 associated with test heads $a$ being located on the opposite side of the diameter 12.1 from the mechanism 15 associated with the test heads $b$. The base members 10 and 11, the head piece 16 and the tilting lever mechanism 15 of the two test system carriers 10, 11 are in this manner disposed virtually point-symmetrically to each other and statically balanced, as viewed in direction of the nozzle axis $a'$. Point symmetry means that after rotation through 180°, the system A is substantially coincidental with the system B. Within each of the base members 10.1, 11.1 there is a pneumatic drive, which is not shown in detail. By means of such drives, which are well known in the art, the head pieces 16 with the tilting lever mechanisms 15 and the heads $a$ and $b$ fastened thereon can be inserted or withdrawn in radial direction and can therefore be brought into the test position thereof. For a given stoke of the telescopic tube 9, a definite test track or path can be run in this test position, if the test system carrier 1 is rotated in circumferential direction. Then, the test system carrier 1 is displaced a short distance farther axially and the next test path run, whereby particular, meander-shaped or sinusoidal test tracks of a definite density or concentration are obtained. These test paths are described by the testing program in such a manner that they can be run reproducibly. The arrows 10$a$ and 11$a$, respectively, indicate the direction of the radial stroke of the test systems A and B, which can be carried out by the pneumatic piston systems 10.3 and 11.3. The base members 10.1 and 11.1 can be fastened in an accurately adjusted position by a clamping plate 17 and clamping screws 17.1.

Figure 2:
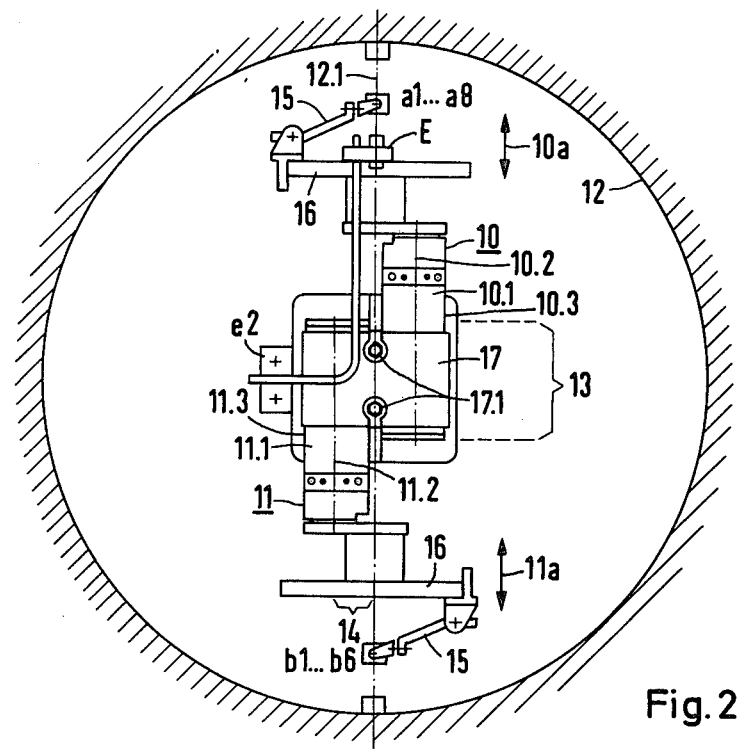
FIG. 2 is a diagrammatic side elevational view of the test system carrier of FIG. 1 as seen from the right-hand side of FIG. 1 and taken in the direction of the nozzle axis.

To fasten the base members 10.1, 11.1 in different adjustment positions depending upon the size of the nozzle diameter, several recesses 180 (FIG. 1) are provided of the base member 1.1 of the test system carrier at different radial distances from the axis $a'$, so that the base members 10.1, 11.1 can be fastened in the respective positions thereof without readjustment. The ultrasonic eye E is disposed at the front end of the test system carrier 1 to center the latter within the nozzle bore 12. The ultrasonic eye E is fastened to the end of the radial arm $e1$ which is bent off at a right angle and fastened to a clamping member $e2$, and which can be swung with the test system carrier 1 about the axis $a'$ i.e. in circumferential direction. The clamping member $e2$ is supported by two guide rods $e3$, $e4$ in a guide body $e5$, not shown in detail so as to be movable in axial direction, a pneumatic driving mechanism with piston and cylinder being associated with the linkage $e3$. In this way the ultrasonic eye can be run, as shown by the double-headed arrow $e'$, from the inserted position E1 to a withdrawn position E2, for example, as is indicated by the dashed lines. The ultrasonic eye E can be adjusted in both coordinate directions to the desired position, and more specifically, by moving the ultrasonic eye E at the connection thereof to the arm $e1$ and by moving the arm $e1$ in the mounting thereof, the ultrasonic eye being secured after adjustment by clamping the same to the arm $e1$ and between $e1/e2$ by clamping the arm $e1$ to the clamping member $e2$, as shown in FIG. 2. It is essential that the ultrasonic eye E be insertable into the nozzle bore 12. In this manner, the test system carrier 1 with the telescopic tube 9 can be brought into the exact centered position before the ultrasonic testing systems A, B, C, D proper are run into the test positions thereof.

The test system C for testing the nozzle corners is formed of an ultrasonic test head $C_o$ attached to a gimballed tilting lever mechanism 15; an intermediate member 18; a drag lever 19 proper with an outer lever arm 19$a$; an inner lever arm 19$b$; a pneumatic drive 20 as well as a radial extension 21 which is fastened to the base member 1.1 of the test system carrier 1 and takes up the rotating bearing 20.1 of the drag lever 19. As the doubleheaded arrow 18$a$ indicates, the intermediate piece 18 can be fastened so as to be adjustable relative to the drag lever 19 in radial direction in order to make allowance for different nozzle bore diameters. As is evident, both the fulcrum 19$c$ and the pivot bearing 20.1 are eccentric to the axis 9' of the telescopic tube, so that there is no mutual obstruction of the test system C and the yet to be explained test system D during the tilting operation. The inner lever arm 19$b$ forms an angle relative to a longitudinal lever axis 19$d$ of the outer lever arm 19$a$ in such a manner that the maximum torque of the tilting drive 20 lies in the tilting angle range $\alpha$, substantially in the middle of that range. The angle $\alpha$ sweeps over a tilting range of the drag lever 19 which extends from the folded-up rest position C' thereof shown in phantom, to the extreme operating position thereof, indicated by the dot-dash line C" forming one of the legs which define the angle $\alpha$. The tilting drive 20 is a pneumatic cylinder-and-piston system, wherein the rotating bearing 20.1 forms a piston rod which is linked at 19$e$ to the drag lever 19. The housing of the tilting drive 20 and therewith the cylinder are secured to the base member 1.1 of the test system carrier 1 at fastening points 20.2. Pneumatic control lines 20.3 for the tilting drive 20 are also shown in FIG. 1.

The test system D is formed in principle of a similar tilting lever system as the test system C, for which reason functionally similar parts are identified by the same reference characters, with the addition of a prime, however. The difference between the test systems C and D is that the test system D serves for determining longitudinal faults in the nozzle seam 2. In addition, this test system D, as a universal system which should be usable for outlet nozzles 5 as well as for inlet nozzles 6, must take special conditions into consideration. The test system D has two test heads i.e. a radially outer test head $d1$ and an inner test head $d2$ lying on a smaller diameter. As is apparent, the inner test head $d2$ serves for scanning the outlet nozzle bulge or bead 5.1, and has either an extremely shortened intermediate member 18' or, in fact, has none at all. The outer test head $d1$ serves for scanning test tracks of a recessed region 5.2 which lies on a larger diameter than that of the test tracks of the test head $d2$ on the bulge region 5.1. As will be described hereinafter, the test head $d1$ can also serve for performing the longitudinal-fault test for inlet nozzles 6. Ultrasonic cones of rays 210 and 220 are indicated for both test heads $d1$ and $d2$, respectively. The rays penetrate the pressure vessel wall and strike the regions of the nozzle seam 2 to be examined. The inner lever arm 19$b'$ forms an angle $\delta$ with the longitudinal axis 19$d'$, and the entire tilting range extends through an angle $\alpha'$. The pneumatic drive 20' is formed of a piston and cylinder system which, in comparison to the system 20, deviates from the vertical by an angle $\alpha$; this is related to the fact that the drive 20 is fastened at the base member 1.1 so as to be axially shifted relative to the drive 20 and, for a given cranking or angular offset $\delta$, also this drive 20' should deliver the maximal torque thereof in the operating tilting range of the system D. The double-headed arrows 18$a'$ again indicate the adjustability of the intermediate members 18' for adapting or accommodating the test heads $d1$ and $d2$ to different test-track diameters. Curved double-headed arrows 19$f$ and 19$f'$, as also the tilting angles $\alpha$ and $\alpha'$, indicate the tiltability of the drag levers 19 and 19'.

Figure 5:
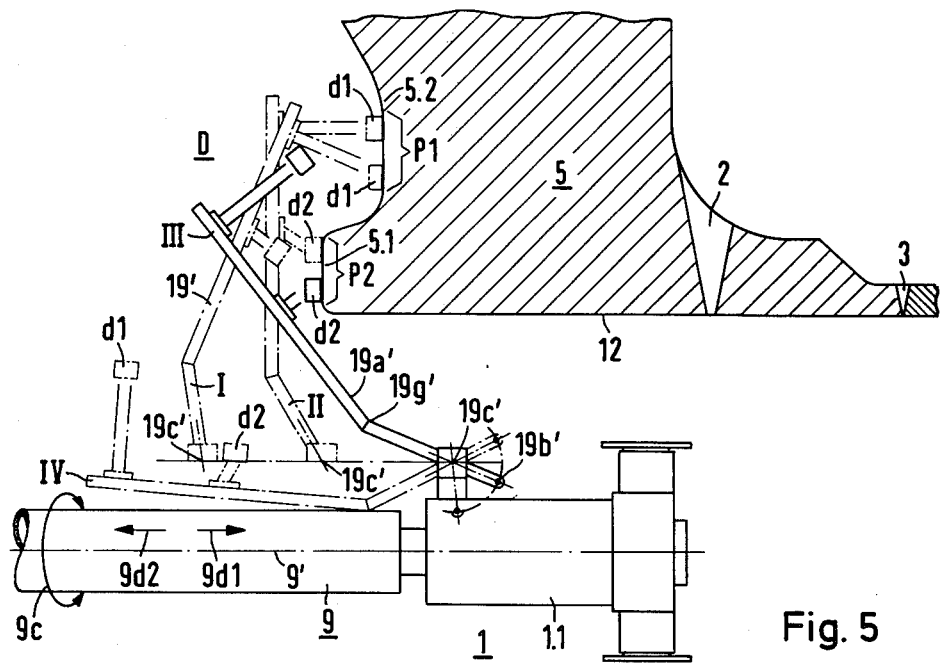
FIG. 5 is a fragmentary view of FIG. 1 showing individual phases of the motion of the drag lever of the test system carrier serving for longitudinal-fault testing of half the cross section of an outlet nozzle.

It should further be mentioned that the drag levers 19 and 19' are provided with the angular offsets or crankings 19g and 19g' so that the drag levers 19 and 19' do not collide with the nozzle corners when they travel around the latter. Before the test system carrier 1 begins its testing program, it is first centered by means of the ultrasonic eye E, for which purpose the ultrasonic eye E on the radial arm e1 thereof is inserted into the nozzle by means of the linkages e3 and e4, so that the necessary correction signals are obtained. After the test system carrier 1 has been properly oriented, it can be moved into the test position, with the systems A and B inserted and the systems C and D folded up (positions C', D'). FIG. 5 shows the motion cycle for the test system D in four time-sequential instantaneous views or phases of motion I to IV. In position I, the fulcrum $19c'$ of the drag lever 19' is in front of the nozzle bore 12 yet and makes contact initially only with the test head $d1$ for scanning the test tracks P1 in the nozzle area 5.2. The test system carrier is slowly rotated by the telescopic tube 9 about the axis 9', so that the entire peripheral area can be scanned. If the drag lever fulcrum $19c'$ is shifted in the direction represented by the arrow $9d1$ i.e. in direction toward position II, the test head $d1$ can be shifted in direction toward test tracks of larger diameter, the test track of different diameter being respectively scanned by the rotation of the test system carrier 1. In position II, the test head $d2$ engages the test area P2 of the nozzle region 5.1, while the test head $d1$ continues to make contact with the area P1; in this position II, the areas P1 and P2 can be tested simultaneously. If the drag lever 19' with its fulcrum $19c'$ is axially shifted farther in the direction $9d1$ i.e. in direction toward position III, the test head $d2$ can be moved to test tracks of smaller diameter; simultaneously, the test head $d1$ has completed its testing program and has already been lifted in position III. Position III shows the final phase of the test head $d2$ in the test zone P2. Upon further axial displacement, the tilting angle $\alpha'$ (see FIG. 1) is shifted by the tilting drive 20' (not shown in FIG. 5) in such a manner that the drag lever 19' moves into the folded-up position IV. In the latter position, the test system carrier 1 can be inserted farther into the nozzle bore 12 to carry out the testing program of the system A and B thereof without obstruction by the drag lever 19', since the latter is located with all its parts on diameters that are smaller than the inner diameter of the nozzle. System C, of course, must also be folded in, because the same considerations apply to this system.

Figure 4:
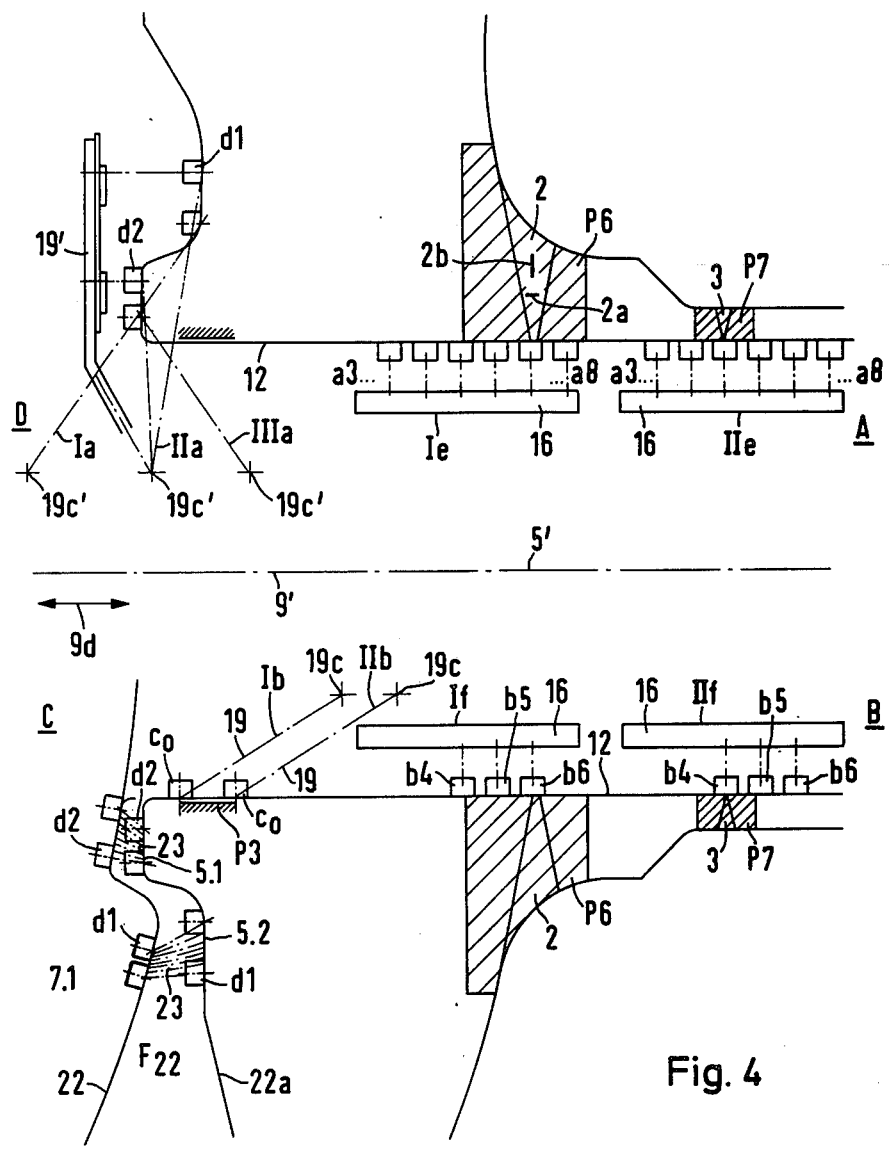
FIG. 4 is a view similar to that of FIG. 3 showing individual phases of the motion of selected parts of the test system carrier during ultrasonic testing of an outlet nozzle.

FIG. 4 once more shows, in the upper half thereof, in a more diagrammatic presentation, the test system D and, more specifically, three successive positions I$a$, II$a$ and III$a$ thereof; these positions I$a$, II$a$ and III$a$ correspond to the respective Positions I, II and III in FIG. 5; however, the drag lever 19' is partially shown with the contours thereof in position II$a$ only; in the other positions I$a$ and III$a$ thereof, only the fulcrum $19c'$ of the drag lever 19', the test head $d1$ or $d2$, respectively, and a connecting line from the respective test head to the drag lever fulcrum $19c'$ are shown. The lower half of FIG. 4 shows the 0°- and 180°-cross-sectional planes as well as a cross sectional view in the diametral plane of the nozzle in a position rotated 90° about the telescope axis 9' or the nozzle axis 5', both of which coincide. It is apparent that the outline or contour 22 of the 90° and 270°-cross-sectional plane or position is moved up ahead of the outline 22$a$ by an area $F_{22}$ in direction toward the interior of the reactor 7.1. The contour 22 represents the inner periphery of the reactor pressure vessel in the plane normal to the axis of the nozzle bores, and it is therefore substantially circular. For the testing process this means that, in scanning the approximately circular test tracks with the aid of the drag levers 19 and 19' about the telescope axis 9', a more-or-less springback or yielding of the drag levers 19 and 19' is necessary within the spring travel path of extensions 19$h$ and 19$h'$ of the respective drag levers 19 and 19' (see FIG. 1) which carry the test heads. It has been found, however, that it is even more advantageous to carry out this yielding pneumatically in adapting or accommodating to the test track contour i.e. the pneumatic drive pressure in the drive 20 and 20' is selected so that this drive permits a springy or resilient action of the entire drag lever 19 or 19' about the fulcrum $19c$ or $19c'$, respectively, thereof. The excursion paths 23 for the test heads $d1$ and $d2$ are obtained if the drag lever 19' is rotated through 360°. In the lower half of FIG. 4, there are also shown two positions I$b$ and II$b$ for the drag lever 19 and its test head $c_O$. These positions I$b$ and II$b$ are obtained when the test system C scans the test region P3 i.e. the cladding at the inner periphery of the nozzle zone 5.1.

Figure 3:
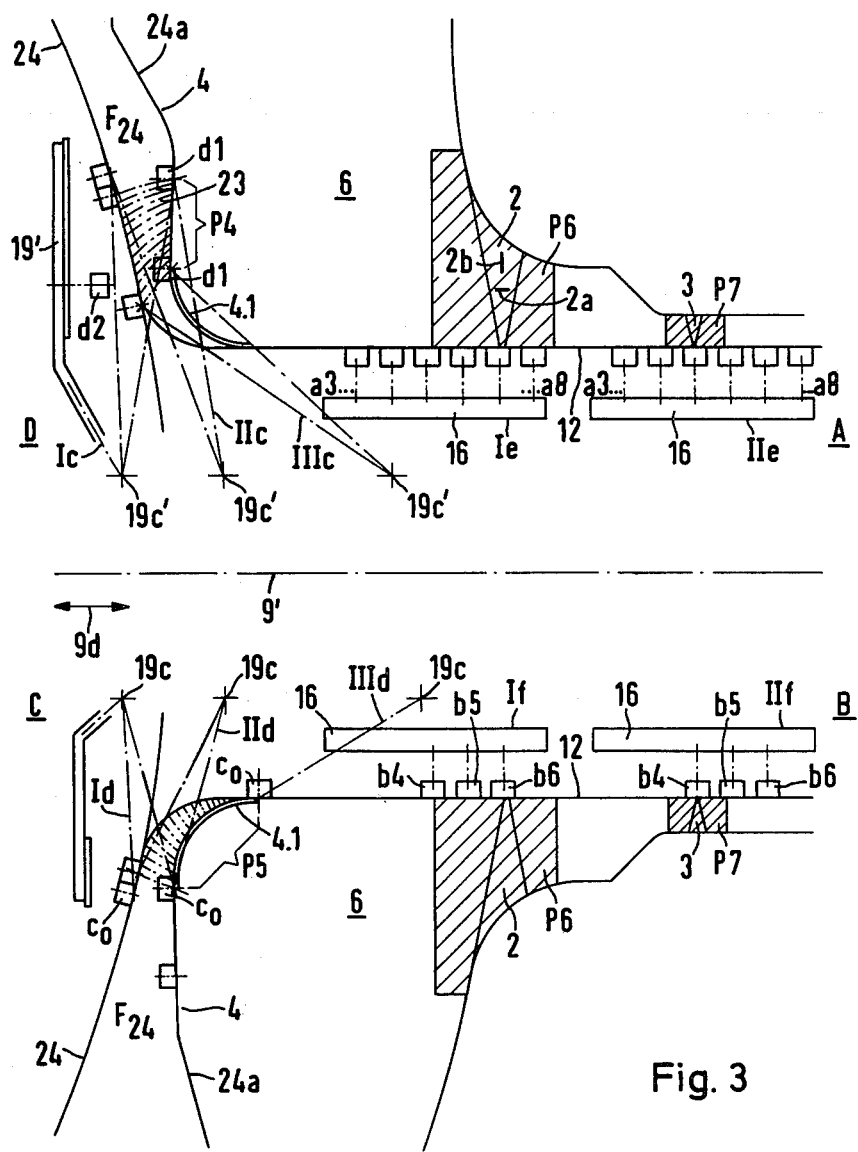
FIG. 3 is a fragmentary view of FIG. 1 showing individual phases of the motion of selected parts of the test system carrier during ultrasonic testing of an inlet nozzle.

FIG. 3 illustrates that the test system D is also used for longitudinal-fault tests in input nozzles, in an area such as the inlet nozzle 6. Specifically, this is done with the test head $d1$ thereof. In the upper half of FIG. 3, again three successive positions of the drag lever 19', namely the positions I$c$, II$c$, III$c$ are shown. Also shown are corresponding, axially displaced positions of the fulcrum $19c'$ of the drag lever 19'. It is apparent that the test system D uses only the outer test heads $d1$ for scanning the test tracks P4 in the region 4.1 of the inlet nozzle 4. In addition to the contour for the 0°- and 180°-position, the contour for the 90°- and 270°-position is also shown and identified by the reference numeral 24. The area $F_{24}$ is formed between the contour 24 and the 0°/180°-contour 24$a$ so that here also a spring travel path 23 for the drag levers 19' or their test heads $d1$, respectively, is obtained. In the lower half of FIG. 3, the test system C is shown in three different positions in scanning the test tracks P5 of the nozzle corner region 4.1 and, specifically, in the positions I$d$, II$d$, III$d$. In the latter positions, the test head $c_O$ can be brought into contact successively with the test tracks P5 of the end face of the nozzle, the nozzle corner and the inner periphery of the nozzle, as is readily apparent. The corresponding circular tracks can be scanned in each of the positions I$d$, II$d$ and III$d$ by rotation of the test system carrier 1. These are not exactly circular tracks because of the differences between the contours 24$a$ and 24, but they are accurately reproducible because of the defined travel program.

The construction of the test heads $d1$, $d2$ and $c_O$ will not be discussed herein in detail as it is of no concern to the invention of the instant application; they are conventional ultrasonic test heads with a transmitter and receiver, the ultrasonic wave emitted by the transmitter being reflected in such a manner at the boundary layers of the material to be examined, that certain norm or standard signals are obtained for fault-free material. The pattern changes, however, if a material fault, such as incipient cracks or so-called circular disk reflectors, is present, hereby generating a signal deviating from the norm or standard signal in the receiver. In the case of the test heads $d1$ and $d2$, a great penetration depth is called for, since they must penetrate the entire vessel wall (see FIG. 1) while, in the case of the test head $c_O$, only the cladding zones 4.1 located immediately under the test head $c_O$ must be tested for incipient cracks.

The foregoing explanations apply analogously to the test systems A and B, which are shown in the upper half of FIG. 3 in the two positions I$e$, II$e$ of the test system A and in the lower half of FIG. 3, in the two positions I$f$, II$f$ of the test system B. Test regions P6 are to be examined in the vicinity of the nozzle seam 2 and test regions P7 in the vicinity of the pipe connection seam 3, both test regions P6 and P7 being shown in shading. Contrary to FIG. 1, in FIGS. 3 and 4, the test system A is shown with only six test heads $a3$ to $a8$, and the test system B with only three test heads $b4$ to $b6$, thereby indicating that a larger or smaller number of test heads can be used, depending upon the test requirements. The test of the inner periphery of a nozzle, such as the outlet in FIG. 4, with the systems A and B for transversal faults and incipient cracks, corresponds to the test of an inlet nozzle as in FIG. 3. Therefore, the following explanations for FIG. 3 apply to FIG. 4 as well, and, furthermore, in both FIGS. 3 and 4, the same reference characters are used for similar features. It is apparent that, in the position I$e$, the test heads $a6$ to $a8$ are located in the test region P6, i.e. they have been brought hydraulically to the inner periphery 12 of the nozzle. In the lower half of FIG. 3, the test heads $b4$ to $b6$ of the system B are in the testing position; these test heads $b4$ to $b6$ are slightly displaced axially relative to the first mentioned test heads $a6$ to $a8$, so that with the two systems A and B, a network of very narrow test tracks can be scanned while testing simultaneously. The test heads $a3$ to $a8$ in the test system A are provided for the pipe connection seam test of test region P7. However, in position II$e$, only the test heads $a4$ to $a6$ are located in the test region P7. In the test system B, the test heads $b4$ to $b6$ are provided for the pipe connection seam test of the test region P7. However, in the position II$f$, the test head $b4$ happens to be in the test region P7.

If the test system carrier 1 has scanned the test tracks P1 to P7 with all the test systems A to D thereof, it is removed from the nozzle bore in direction of the telescope axis 9' (arrow 9$d$); the telescope arm is then rotated by the central-mast manipulator in accordance with arrow 9$b$ in the horizontal plane through an angle sufficient to place it in the correct position for insertion into the next nozzle bore. Thereupon, it is initially centered, and the testing process is repeated as explained hereinabove.

Figure 6A:
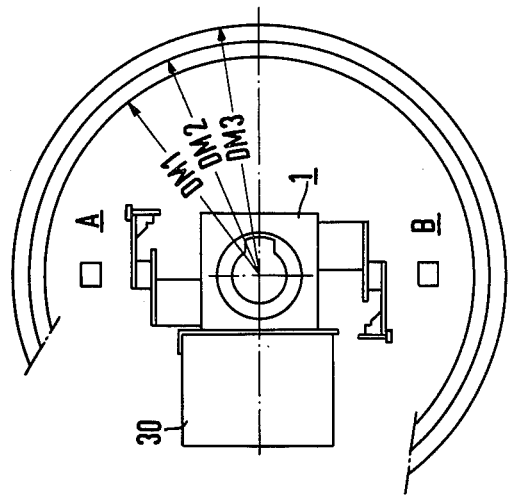
FIG. 6a is a diagrammatic front elevational view of FIG. 6.
Figure 6:
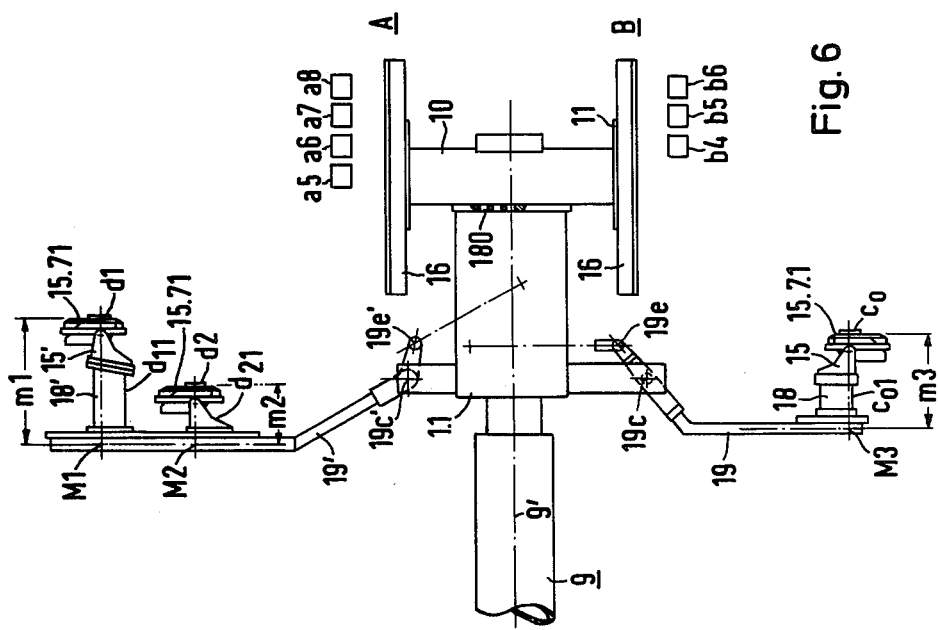
FIG. 6 is a fragmentary view of FIG. 1 showing the test heads in somewhat greater detail.

FIGS. 6 and 6$a$ show highly diagrammatic views of the test system carrier 1 showing the base members 10 and 11 of the systems A and B. FIG. 6$a$ also shows a distributor box 30. In addition, the adjustability of the systems A and B to three different test track diameters DM1, DM2 and DM3 according to the elongated-hole setting 180 is illustrated. Only the test heads $d1$, $d2$ and $c_O$ with their associated tilting lever mechanisms 15' and 15 and the intermediate members 18' and 18 are shown in somewhat greater detail.

Figure 7:
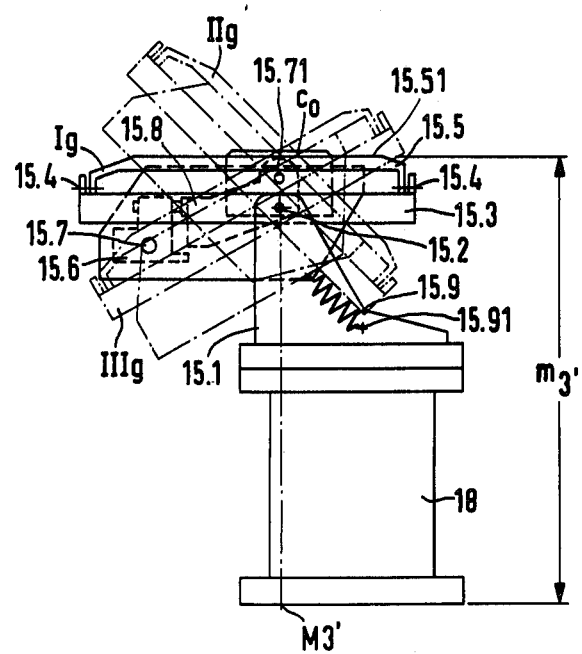
FIG. 7 is an enlarged fragmentary view of FIG. 1 showing the cardanic or gimbal suspension of an individual drag lever test head.
Figure 8:
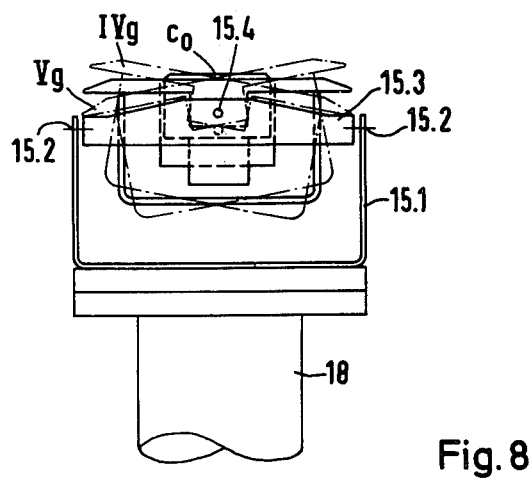
FIG. 8 is a fragmentary front elevational view of FIG. 7.

A detailed view of the test head $c_O$ from FIG. 6, and its tilting lever system 15, and intermediate member 18, is shown in FIGS. 7 and 8 in order to illustrate the gimballed or cardanic suspension. At the intermediate member 18, a support fork 15.1 is mounted. An intermediate bracket 15.3 is hinged in pivots 15.2. The intermediate bracket 15.3, in turn, is provided with second pivots 15.4, in which a slide carriage 15.5, hereinafter simply called the slide, is supported. Inside the slide 15.5, and more specifically mounted on a pivot shaft 15.7 which forms a fulcrum for the test head spring linkage, there is a pillow block and a non-illustrated torsion spring. The test head $c_O$ proper is fastened to the pillow block 15.6 by means of the shaft pivot 15.7, and by means of a fork 15.8 to a second pivot shaft 15.71 which extends crosswise to the pivot shaft 15.7. A coil spring 15.9, which is hooked with one end thereof to a point 15.91 on the support fork 15.1, engages the slide 15.5 with the other end thereof. In this manner, the slide 15.5 is able to assume the positions II$g$ and III$g$ thereof illustrated in phantom, the starting position I$g$ thereof being shown in solid lines. The slide 15.5 is thus able to adapt to unevennesses and inclinations of the test tracks, as indicated also in FIG. 8 by the positions IV$g$ and V$g$.

In FIG. 8, the test head $C_o$ is only roughly indicated for greater clarity, and the parts 15.6, 15.7 and 15.8 have been omitted. It is important for the reproducibility of the test tracks that the dimensions or spacings $m_1$, $m_2$, $m_3$ and $m_3'$ (see also FIG. 6) remain constant under all circumstances. These are given by the distance of the slide contact surfaces 15.71 from their angle-lever base point M1 or M2 or M3 or M3', respectively, the angle levers being identified by reference characters $d_{11}$, $d_{21}$ and $d_{01}$. The slide 15.5 adjusts itself, with the gimballed suspension 15.2, 15.4 thereof to the test track plane, and within the slide 15.5, the test head $C_o$, with its gimballed suspension 15.7, 15.7.1, can follow the exact compound curve of the test track, spring-loaded by the pillow block 15.6 and the torsion spring. This double-gimballed suspension of the slide carriage 15.5 and the test head $C_o$ therefore ensures that the test heads follow easily without affecting the contact pressure and the contact area of the test head $c_O$. The other test heads $d1$ and $d2$, and the accurate reproducibility of the compound curves traced are also unaffected. The gimballed test head suspension shown in FIGS. 7 and 8 is also used for the test heads $a1$ to $a8$ and $b1$ to $b6$ of the systems A and B, but with the difference that the slide 15.5 need not be suspended in gimbals, since the test tracks are simple circular tracks. A separate illustration of this last-mentioned variant has therefore been dispensed with. In view of the function of the slide 15.5, it may also be called a slide shoe.

There are claimed:

1. Test system carrier for ultrasonic testing of nozzle seams, pipe connection seams and nozzle corners in pressure vessels, the carrier being supported at the end of a telescopic tube for executing stroke and rotary motions in or about the axis of the nozzle, the telescopic tube being adjustably mounted on the central mast of a central-mast manipulator so as to be adjustable in elevation and rotatable about the axis of the central mast as well as about its own axis comprising, in combination, inner-periphery test-head carrier means for ultrasonically testing seams formed in the nozzle and seams between pipe connections and the nozzle as well as zones adjacent thereto; a tiltable test-head carrier having at least one drag lever pivotally attached to the test system carrier, said drag lever having an inner and an outer lever arm, tilting drive means coupled to said inner lever arm for tilting the same, test-head means carried by said outer lever for testing the nozzle corners, said drag lever being successively movable so as to bring said test-head means into contact with surfaces at the end of the nozzle, the corner of the nozzle and the inner periphery of the nozzle and movable in test tracks within the entire respective peripheral angle range thereof; said test head means being engageable with the respective test tracks to be contacted, means for telescoping said telescopic tube so as to shift the pivot axis of said drag lever axially away from the telescoping tube, said drag lever having an angular position with respect to the telescoping tube that is variable for contacting the respective test tracks, said drag lever being controllably movable into an inward folded-up rest position wherein said arms thereof are disposed on a diameter that is smaller than the daimeter of the inner periphery of the nozzle so that the test system carrier with said inner-periphery test-head carrier is axially displaceable unobstructedly through the nozzle.

2. Test system carrier according to claim 1 including another drag lever having test head means for testing longitudinal faults, said last-mentioned test head means being movable into contact with the ends of the nozzle and movable over test tracks in peripheral direction of the nozzle, said test tracks being disposed over entire annular zones of the end of the nozzle lying in a projection of the nozzle seams.

3. Test system carrier according to claim 1 including an ultrasonic centering eye being disposable within the bore of the nozzle at a forward end of the test system carrier for centering the latter within the nozzle bore, said eye being mounted on a free end of a radial arm forming part of the test system carrier and being pivotable in peripheral direction, linkage means for inserting said eye into the nozzle bore forward of other test systems of the test system carrier so that said other test systems are displaceable into the test position thereof only if the axis of the test system carrier and the axis of the telescoping tube are centered within the nozzle bore.

4. Test system carrier according to claim 1 wherein the pivot axis of said drag lever is disposed respectively eccentric to the axis of the telescoping tube and is formed of a radial projection secured to the outer periphery of a housing for the test system carrier, and including a compressed-air cylinder fastened to said housing for the test system carrier, said cylinder having a drive member linked to said inner lever arm of said drag lever, respectively.

5. Test system carrier according to claim 1 wherein said inner lever arm of said drag lever is disposed at an angle to a longitudinal axis of the drag lever defined by said outer lever arm so that the pivot angle range of said drag lever, which encompasses the operating range and the rest position of said drag lever, is convertible by said tilting drive means in the range of the maximal torque thereof.

6. Test system carrier according to claim 2 wherein said test head means carried by said first-mentioned drag lever comprises at least two universally mounted test heads disposed at different diameters for testing a nozzle contour having two test track zones offset axially and radially from one another, said universally mounted test heads being adapted to test nozzle seams for longitudinal faults.

7. Test system carrier according to claim 1 including a pair of inner-periphery test-head carriers having respective rows of test heads located diametrically opposite one another in the testing position thereof within a nozzle bore, said pair of inner-periphery test-head carriers having respective base members forming a secured part of the test system carrier and being disposed eccentric to the longitudinal axis thereof, said base members extending parallel to and overlapping one another in the diametral direction, said test heads of said rows being associated with different functional groups serving to test the nozzle seam and the seam between the pipe connection and the nozzle.

8. Test system carrier according to claim 1 wherein said test head means comprise a plurality of test heads, and including respective cardanic tilting lever mechanisms whereon said test heads are mounted.

9. Test system carrier according to claim 8 wherein said test heads include inner-periphery test heads, a respective base member having a head member seated at an outer end thereof, the cardanic tilting lever mechanisms for the respective inner-periphery test heads being fastened to the respective base member, said base member, head member and tilting lever mechanism for said inner periphery test heads, as viewed in axial direction of the nozzle, being disposed substantially point-symmetrically to one another and statically balanced.

10. Test system carrier according to claim 8 including a plurality of said drag levers, and wherein said test head means comprise respective test heads for said drag levers, and further including a slide for the respective test heads mounted on a cardanic link of an angle lever, said angle lever having a base point and said slide having a contact surface disposed at a constant spacing, with respect to the neutral position thereof, from said base point, there being no spring travel path between said slide and said base point in said spacing direction, the respective test head being cardanically mounted at said slide, said test head and the respective cardanic mounting thereof being seated on a tilting lever spring-loaded in direction of applied force.

* * * * *